(12) United States Patent
Shahid

(10) Patent No.: US 7,435,816 B2
(45) Date of Patent: Oct. 14, 2008

(54) SYNTHESIS OF SOLANUM GLYCOSIDES

(76) Inventor: Mohammed Shahid, 36 Upper Brook Street, London W1K7QJ (GB)

( * ) Notice: Subject to any disclaimer, the term of this patent is extended or adjusted under 35 U.S.C. 154(b) by 0 days.

(21) Appl. No.: 10/555,038

(22) PCT Filed: Apr. 30, 2004

(86) PCT No.: PCT/EP2004/004629

§ 371 (c)(1),
(2), (4) Date: Apr. 10, 2007

(87) PCT Pub. No.: WO2004/096830

PCT Pub. Date: Nov. 11, 2004

(65) Prior Publication Data

US 2008/0039628 A1    Feb. 14, 2008

(30) Foreign Application Priority Data

Apr. 30, 2003    (EP) .................... 03009725

(51) Int. Cl.
*C07D 491/107*    (2006.01)
*C07J 71/00*    (2006.01)

(52) U.S. Cl. ............... 546/17; 536/5; 536/6.1; 536/18.5; 536/18.6

(58) Field of Classification Search .......... 536/5, 536/6.1, 18.5, 18.6; 546/17
See application file for complete search history.

(56) References Cited

U.S. PATENT DOCUMENTS 6,242,583 B1 * 6/2001 Schmidt et al. ............ 536/4.1

FOREIGN PATENT DOCUMENTS

WO    WO 03/018604 A1    3/2003

OTHER PUBLICATIONS

Awad, L.F., et al., "A Synthesis of 3-*O*-(α-D-Mannopyranosyl)-D-Mannose and Its Protein Conjugate," *Carbohydrate Research* 122:69-79, 1983.

Fewell, A.M., et al., "Interactions Between the Glycoalkaloids Solasonine and Solamargine in Relation to Inhibition of Fungal Growth," *Phytochemistry* 37(4):1007-1011, 1994.

Figueroa-Pérez, S., and V. Vérez-Bencomo, Synthesis of a Sialyl-α-(2→6)-Lactosamine Trisaccharide With a 5-Amino-3-Oxapentyl Spacer Group at C-1$^t$, *Carbohydrate Research* 317:29-38, 1999.

Fürstner, A., et al., "Ring-Closing Alkyne Metathesis. Application to the Total Synthesis of Sophorolipid Lactone," *J. Org. Chem.* 65:8758-8762, 2000.

Li, B., et al., "An Improved Synthesis of the Saponin, Polyphyllin D," *Carbohydrate Research* 331:1-7, 2001.

Sugiyama, S., and J.M. Diakur, "A Convenient Preparation of Glycosyl Chlorides From Aryl/Alkyl Thioglycosides," *Organic Letters* 2(17):2713-2715, 2000.

* cited by examiner

*Primary Examiner*—Charanjit S Aulakh
(74) *Attorney, Agent, or Firm*—Christensen O'Connor Johnson Kindness PLLC

(57) ABSTRACT

The present invention relates to the chemical synthesis of solanum glycosides, in particular to the synthesis of solasonine as well as to novel β-monosaccharide intermediate compounds, of Formula (2), where $R_1$ is a benzylidene, 4-nitrobenzylidene or 4-methoxybenzylidine group, and each $R_2$ independently is a benzoyl, acetyl or pivaloyl group:

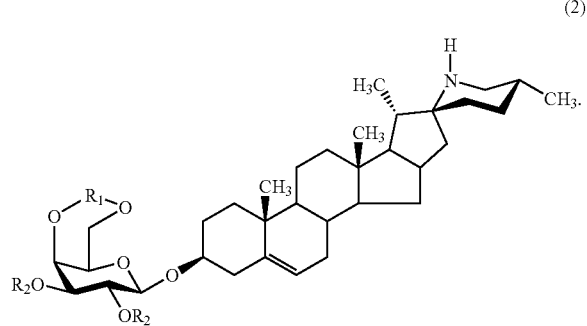

(2)

10 Claims, No Drawings

SYNTHESIS OF SOLANUM GLYCOSIDES

The present invention relates to the chemical synthesis of solanum glycosides, in particular to the synthesis of solasonine as well as to novel β-monosaccharide intermediate compounds.

Solasodine and its glycosides are of considerable interest clinically. They are widely used as starting products for the synthesis of various steroidal drugs, the aglycon solasodine is a source for synthetic cortisone and progesterone.

It is moreover well established that certain naturally occurring conjugate solasodine glycosides have potent antineoplastic properties. Of particular interest are the triglycosides solasonine (22R, 25R)-spiro-5-en-3β-yl-α-L-rhamnopyranosyl-(1->2 gal)-O-p-D-glucopyranosyl-(1->3 gal)-β-D-galactopyranose and solamargine (22R, 25R)-spiro-5-en-3β-yl-α-L-rhamnopyranosyl-(1->2 glu)-α-L-rhamnopyranosyl-(1->4 glu)-β-D-gluco-pyranose. The structures of these triglycosides are shown below:

cosides. The extraction process for making BEC involves homogenizing the fruits of *S. sodomaeum* in a large volume of acetic acid, filtering off the liquid through muslin followed by precipitation of the glycosides with ammonia (Drugs of today (1990), Vol. 26 No. 1, p. 55-58, cancer letters (1991), Vol. 59, p. 183-192). The yield of the solasodine glycoside mixture is very low (approx. 1%). Moreover the individual process steps are not defined to GMP in terms of scale up, definition of yield, composition and product quality.

There is a great need for a cost efficient process that provides the antineoplastically active triglycoside solasonine at high yield with little or no impurities.

Contrary to other steroid ring systems, the steroid skeleton of solasodine contains a very labile nitrogen-containing ring. This aglycon cannot readily be chemically modified while keeping the steroid skeleton intact. In spite of the fact that the aglycon solasodine is readily available, the prior art does not disclose the synthesis of the solasonine using the aglycon material as starting material.

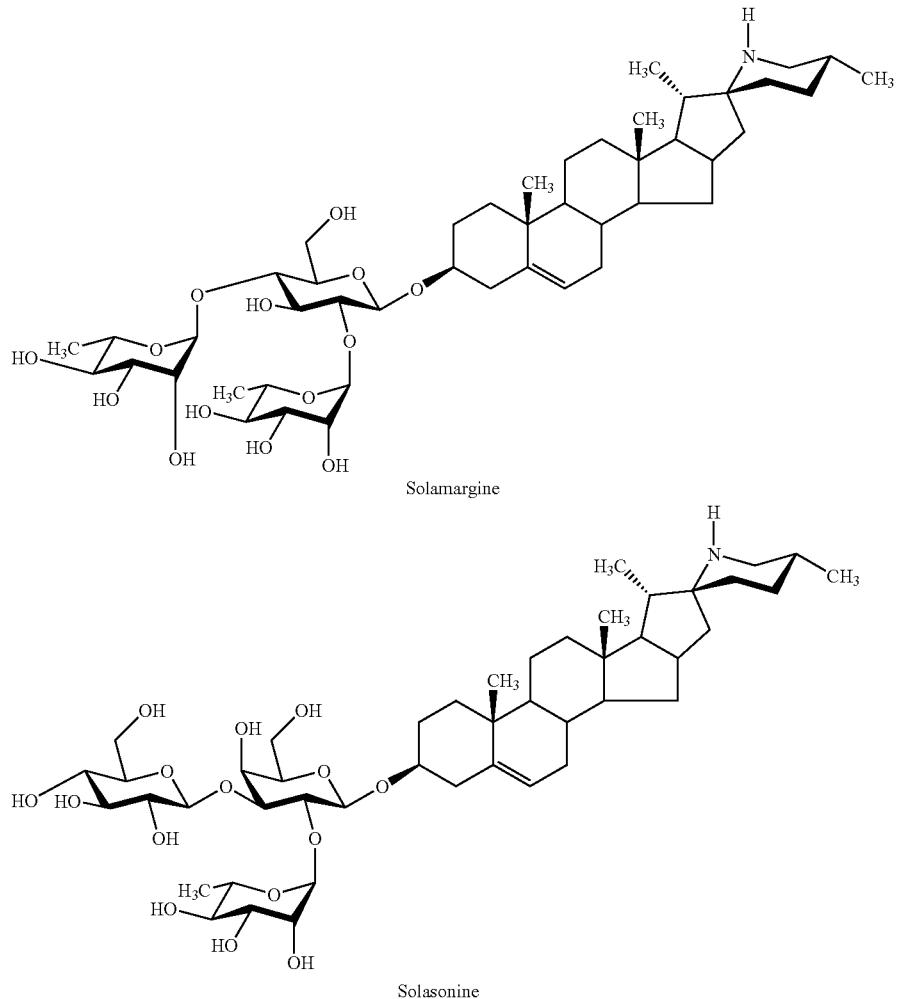

Solamargine

Solasonine

The above triglycosides are conventionally obtained by extraction from a plant source. A commercially available extract of *S. sodomaeum*, commonly referred to as BEC (Drug Future, 1988, vol. 13.8, pages 714-716) is a crude mixture of solamargine, solasonine and their isomeric diglycosides.

The synthesis of solasonine requires the stereoselective glycosylation of solasodine at the relatively unreactive hydroxyl group.

It has been found that solasodine is not compatible with the conventional steroid glycosylation technique. No glycosylation was observed following the treatment of solasodine with tetrabenzoyl α-D-glucopyranosyl trichloroacetimidate and trimethyl-silyl triflate or boron trifluoride dietherate (unpublished results).

The problem underlying the present invention is to provide a cost effective method for the preparation of solasonine.

The present invention resides in the finding that the stereoselective β-glycosylation of solasodine may be achieved in high yields using specific galacto-pyranosyl donors. Preferably the reaction is carried out in the presence of a promoter.

DETAILED DESCRIPTION OF THE INVENTION

It was unexpectedly found that by reacting a D-galacto-pyranosyl donor of the following formula 1

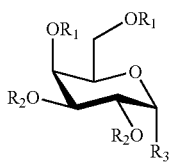

Formula 1

$R_1$ = Benzylidine, 4-nitrobenzylidine or 4-methoxybenzylidine
$R_2$ = Benzoyl, acetyl or pivolyl
$R_3$ = Halogen, SEt or SPh wherein each $R_1$ is the same or different and independently represents a benzylidene, 4-nitrobenzylidene or 4-methoxybenzylidene group each R2 is the same or different and independently represents a benzoyl, acetyl or pivaloyl group and $R_3$ is halogen, SPh or SEt with solasodine the correspondingly protected β-glycoside of formula 2 could be obtained in high yield.

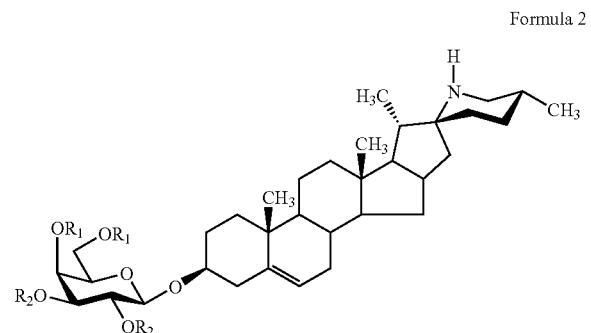

Formula 2

$R_1$ = Benzylidine, 4-nitrobenzylidine or 4-methoxybenzylidine
$R_2$ = Benzoyl, acetyl or pivolyl wherein each $R_1$ is the same or different and independently represents a benzylidene, 4-nitrobenzylidene or 4-methoxybenzylidene group and each $R_2$ is the same or different and independently represents a benzoyl, acetyl or pivaloyl group.

Preferably the reaction is carried out in the presence of a promoter.

Any conventional promoter as used in carbohydrate chemistry may be used.

The following promoters are particularly preferred:

Silver triflate, boron trifluoride diethyl etherate (−10° C.), trimethylsilyl triflate bromide, N-iodosuccinimide, thiomethyl sulfonium triflate.

The reaction is preferably carried out using dichloromethane as the solvent. Preferably the reaction time is 30 min.-1 hr.

The desired end product solasonine may be prepared by partially deprotecting the β-glycoside of formula 2 to give intermediate formula 3(1) and then selectively silylating one of the hydroxyl groups (OH-2 and OH-3) using tert-butyldimethylsilyl chloride, imidazole in DMF at 50° C.

However, due to the small selectivity between the OH-2 and OH-3 hydroxyl groups a mixture of OH-2 and OH-3 silylated protected β-glycosides are formed. The OH-3 silylated protected β-glycoside can mostly be precipitated from the mixture in methanol of the formula 3(2).

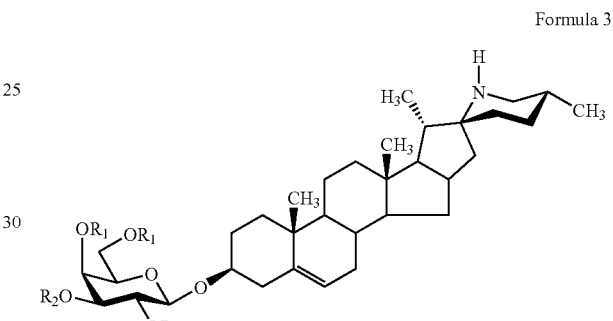

Formula 3

3(1) $R_1$ = Benzylidine, 4-nitrobenzylidine or 4-methoxybenzylidine
  $R_2$ = H
  $R_3$ = H 3(2) R1 = Benzylidine, 4-nitrobenzylidine or 4-methoxybenzylidine
  R2 = Tert butyl silyl
  R3 = H wherein each of $R_1$ is the same or different and represent independently from each other benzylidene, 4-nitrobenzylidene or 4-methoxybenzylidene, $R_2$ is tert-butylsilyl or H and $R_3$ is H.

The OH-3 protected galactose-solasodine adduct is then glycosylated at the OH-2 with a suitable α-L-rhamnopyranosyl donor.

Suitable rhamnose donors include tri-O-benzolyl-α-rhamnopyranosly, tri-O-pivoloyl-L-rhamnopyranosyl, or tri-O-acetyl-4-L-rhamnopyranosyl bromides of formula 4

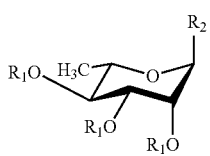

Formula 4

$R_1$ = Acetyl, benzoyl or pivolyl
$R_2$ = Halogen, SEt or SPh wherein each of $R_1$ is the same or different and independently represents acetyl, benzoyl or pivaloyl, and $R_2$ is halogen or SEt, SPh Deprotection of the tert-butylsilyl group at the OH-3 position using tetrabutylammonium flouride in THF and glycosidation with a suitable α-D-glucopyranosly donor, wherein the D-gluco-pyranosyl donor is tetra-O-benzoyl-α-D-glucopyranosyl bromide, tetra-O-acetyl-α-D-glucopyranosyl bromide or tetra-O-pivoloyl-α-D-glucopyranosyl bromide, or a thio-glycoside of the general formula 5

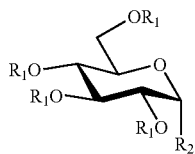

Formula 5

$R_1$ = Acetyl, benzoyl or pivolyl
$R_2$ = Halogen, SEt or SPh wherein each of $R_1$ is the same or different an independently represents acetyl, benzoyl or pivaloyl and $R_2$ is halogen, SEt, SPh gives a fully protected solasonine of formula 6(1).

wherein each $R_1$ is the same or different and independently represents benzylidene, 4-nitrobenzyilidene or 4-methoxybenzylidene and each $R_2$ are the same or different and independently represent acetyl, benzoyl or pivaloyl.

The protected solasonine formula 6(1) may be de-acetalised using aqueous acetic acid at 70° C. and de-esterified using sodium methoxide in methanol/dichloromethane mixture to give the fully deprotected solasonine formula 6(2) where in $R_1$ and $R_2$ are H.

The invention claimed is:

1. A galactose-solasodine conjugate of the general formula 2

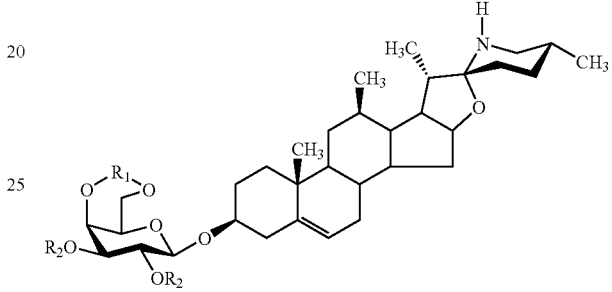

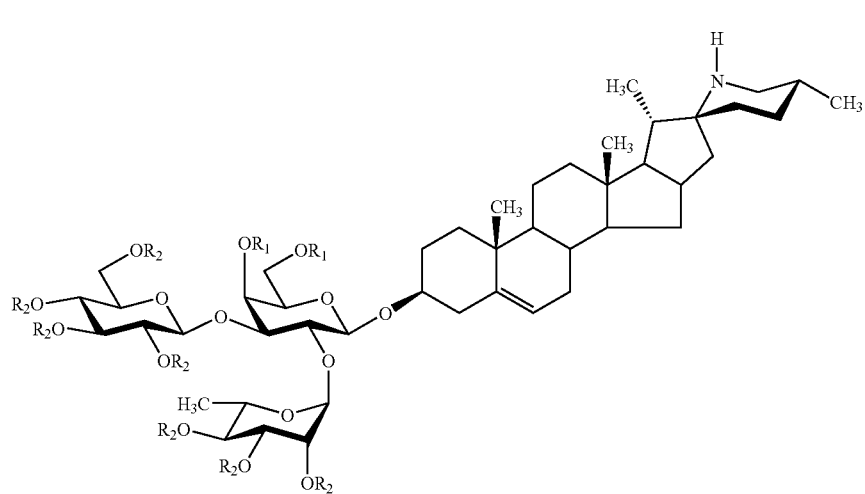

Formula 6

6(1) $R_1$ = Benzylidine, 4-nitrobenzylidine or 4-methoxybenzylidine
$R_2$ = Benzoyl, acetyl or pivolyl

6(2) $R_1$ = $R_2$ = H wherein R₁ is benzylidene, 4-nitrobenzylidene or 4-methoxybenzylidene, and each R₂ independently is benzoyl, acetyl or pivaloyl.

2. A method for the preparation of the galactose-solasodine conjugate as defined in claim 1, comprising the reaction of solasodine with a galactopyranosyl donor of general formula 1

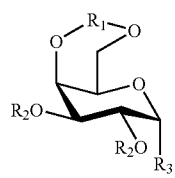

(1)

wherein each R₂ independently is benzoyl, acetyl or pivaloyl, R₁ is benzylidene, 4-nitrobenzylidene, or 4-methoxybenzylidene, and R₃ is halogen, SEt or SPh.

3. A method for the preparation of solasonine comprising the silylation of the diol of formula 3(1) to give a selectively silylated product in the OH-3 position of formula 3(2)

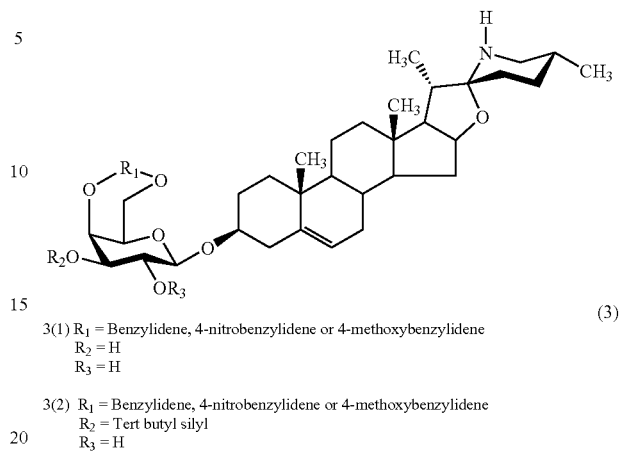

(3)

3(1) R₁ = Benzylidene, 4-nitrobenzylidene or 4-methoxybenzylidene
R₂ = H
R₃ = H

3(2) R₁ = Benzylidene, 4-nitrobenzylidene or 4-methoxybenzylidene
R₂ = Tert butyl silyl
R₃ = H wherein R₁ is a benzilidene, 4-nitrobenzilidene, or 4-methoxybenzylidene acetal protecting group, obtained by glycosylation of OH-2 with an α-L-rhamnopyranosyl donor, followed by deprotection of the silyl group on the hydroxyl OH-3 and a further glycosylation of the hydroxyl OH-3 with an α-D-glucopyranosyl donor to yield the protected solasonine of formula 6(1), which is de-acetalised and de-esterified to yield a solasonine of formula 6(2)

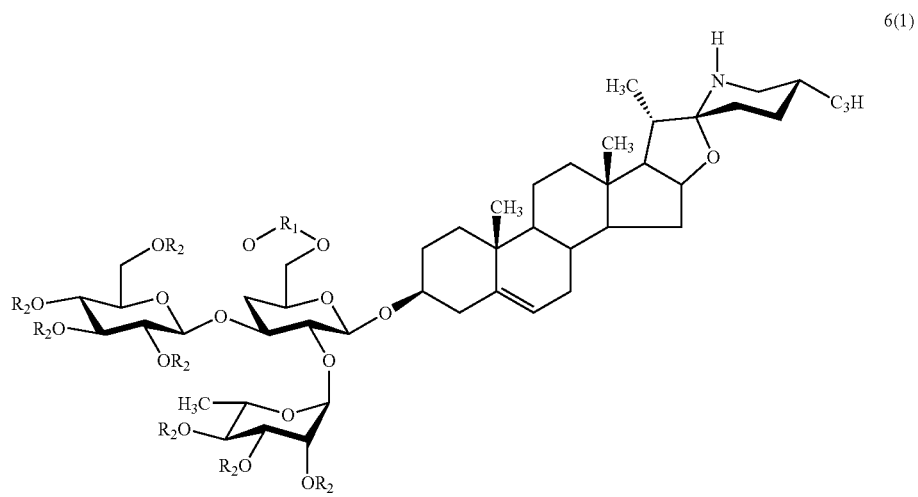

6(1)

-continued

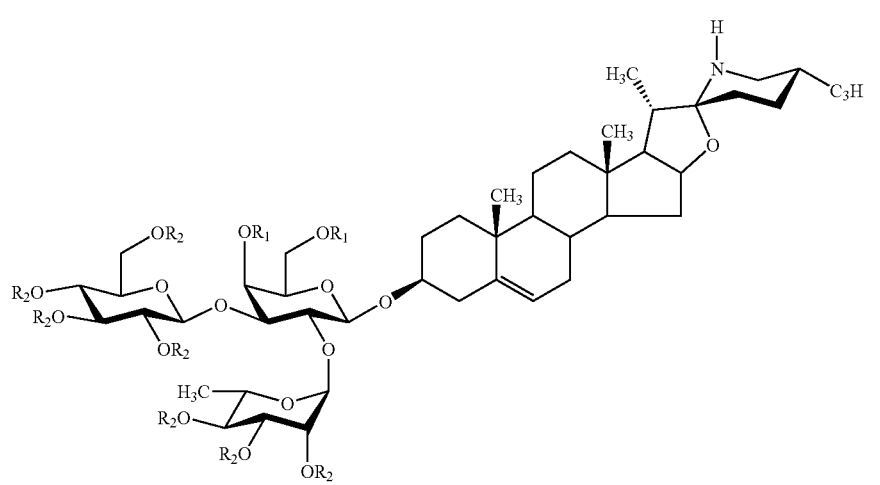

6(1) R₁ = Benzylidene, 4-nitrobenzylidene or 4-methoxybenzylidene
R₂ = Benzoyl, acetyl or pivolyl

6(2) R₁ = R₂ = H

4. The method according to claim 3, wherein the D-glucopyranosyl donor is tetra-O-benzoyl-α-D-glucopyranosyl bromide, tetra-O-acetyl-α-D-glucopyranosyl bromide or tetra-O-pivaloyl-α-D-glucopyranosyl bromide.

5. The method according to claim 2 or claim 3, wherein the reaction of solasodine with a galactopyranosyl donor is carried out in the presence of a promoter selected from silver triflate, boron trifluoride diethyl etherate, trimethylsilyl triflate bromide, N-iodosuccinimide, or dimethyl thiomethyl sulfonium triflate.

6. The method of claim 3, wherein the protected glycoside is deprotected in methanol-dichloromethane solution by treatment with sodium methoxide, followed by neutralization with a mild acid ion-exchange resin.

7. The method of claim 3, wherein the hydroxyl groups at positions 4 and 6 are protected by acetalisation with Benzaldehyde dimethoxy acetal in DMF and a catalytic amount of para-toluene sulphonic acid.

8. The method of claim 3, wherein the rhamnose donor is tri-O-benzoyl-α-L-rhamnopyranosyl bromide, or a glycoside of the general formula 4

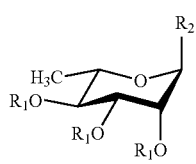 (4)

wherein each $R_1$ independently is benzoyl, acetyl or pivaloyl; and $R_2$ is halogen, SEt or SPh.

9. The method of claim 3, wherein the α-D-glucopyranosyl donor is tetra-O-benzoyl-α-D-glucopyranosyl bromide or a glycoside of the general formula 5

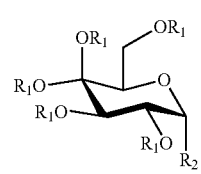 (5)

wherein each $R_1$ is benzoyl, acetyl or pivaloyl; and $R_2$ is SEt, SPh or halogen.

10. The method of claim 3, wherein the protected solasonine is de-acetalised and de-esterified by treatment with 80% acetic and then sodium methoxide solution in methanol-dichloromethane, followed by neutralization with a mild acid ion-exchange resin.

* * * * *